(12) United States Patent
Teller et al.

(10) Patent No.: US 7,691,285 B2
(45) Date of Patent: *Apr. 6, 2010

(54) MAGNETIC NANOPARTICLES HAVING IMPROVED MAGNETIC PROPERTIES

(75) Inventors: Joachim Teller, Mistorf (DE); Fritz Westphal, Poppendorf (DE); Cordula Gruettner, Guestrow (DE)

(73) Assignee: Micromod Partikeltechnologie GmbH, Rostock (DE)

( * ) Notice: Subject to any disclaimer, the term of this patent is extended or adjusted under 35 U.S.C. 154(b) by 153 days.

This patent is subject to a terminal disclaimer.

(21) Appl. No.: 10/564,228

(22) PCT Filed: Jul. 9, 2004

(86) PCT No.: PCT/EP2004/007539

§ 371 (c)(1),
(2), (4) Date: Feb. 8, 2006

(87) PCT Pub. No.: WO2005/006356

PCT Pub. Date: Jan. 20, 2005

(65) Prior Publication Data

US 2006/0163526 A1 Jul. 27, 2006

(30) Foreign Application Priority Data

Jul. 10, 2003 (DE) .................................. 103 31 439

(51) Int. Cl.
*H01F 1/00* (2006.01)
(52) U.S. Cl. .............. 252/62.54; 252/62.53; 252/62.52; 252/62.56; 977/811; 977/838; 977/830
(58) Field of Classification Search .................. 977/811, 977/838, 830; 252/62.54, 62.53, 62.52, 62.56
See application file for complete search history.

(56) References Cited

U.S. PATENT DOCUMENTS

| | | | |
|---|---|---|---|
| 4,101,435 A | 7/1978 | Hasegawa et al. | |
| 4,280,918 A | 7/1981 | Homola et al. | |
| 4,329,241 A | 5/1982 | Massart | |
| 4,452,773 A | 6/1984 | Molday | |
| 4,501,726 A * | 2/1985 | Schroder et al. | 424/1.37 |
| 4,677,027 A | 6/1987 | Porath et al. | |
| 4,827,945 A | 5/1989 | Groman et al. | |
| 5,034,145 A * | 7/1991 | Leising et al. | 252/62.54 |
| 5,160,725 A | 11/1992 | Pilgrimm | |
| 5,304,364 A | 4/1994 | Costa et al. | |
| 5,358,659 A | 10/1994 | Ziolo | |
| 5,427,767 A | 6/1995 | Kresse et al. | |
| 5,545,395 A | 8/1996 | Tournier et al. | |
| 5,580,692 A | 12/1996 | Lofftus et al. | |
| 5,595,687 A | 1/1997 | Raynolds et al. | |
| 5,635,206 A | 6/1997 | Ganter et al. | |
| 5,667,716 A | 9/1997 | Ziolo et al. | |
| 5,814,687 A | 9/1998 | Kasai et al. | |
| 5,852,076 A | 12/1998 | Serafin et al. | |
| 6,541,039 B1 | 4/2003 | Lesniak et al. | |
| 6,576,221 B1 | 6/2003 | Kresse et al. | |
| 2003/0092029 A1 | 5/2003 | Josephson et al. | |
| 2003/0099954 A1 | 5/2003 | Miltenyi et al. | |

FOREIGN PATENT DOCUMENTS

| | | |
|---|---|---|
| DE | 100 20 376 A1 | 11/2001 |
| EP | 0 699 964 A1 | 3/1996 |
| EP | 0272091 | 10/1998 |
| WO | WO-90/07380 | 7/1990 |
| WO | WO-95/27437 | 10/1995 |
| WO | WO-01/17662 A2 | 3/2001 |
| WO | WO-01/56546 | 9/2001 |
| WO | WO-01/74245 A1 | 10/2001 |
| WO | WO-02/43708 A2 | 6/2002 |

\* cited by examiner

*Primary Examiner*—C. Melissa Koslow
(74) *Attorney, Agent, or Firm*—Jordan and Hamburg LLP

(57) ABSTRACT

The invention relates to a method for producing magnetic nanoparticles which are made of metal oxide-polymer composites and are provided with an increased magnetic mobility, among other things, due the high metal oxide content and the morphological structure thereof. High-pressure homogenization has proven to be a reliable technique for producing the inventive magnetic nanoparticles. According to said technique, the components metal oxide and polymer are processed in a carrier medium. Water is used in most cases at pressures ranging from 500 bar to 1200 bar while using great shearing forces. High pressure homogenization creates a colloidally stable magnetic particle population having a diameter ranging below 200 nm while also resulting in the produced magnetic nanoparticles being provided with greater magnetic moments than the metal oxide used as an initial material at low magnetic field strengths. The inventive particles are particularly suitable for applications in the bioanalytical and diagnostic field, in bioseparation processes, and as a carrier material in high throughput screening.

16 Claims, 1 Drawing Sheet

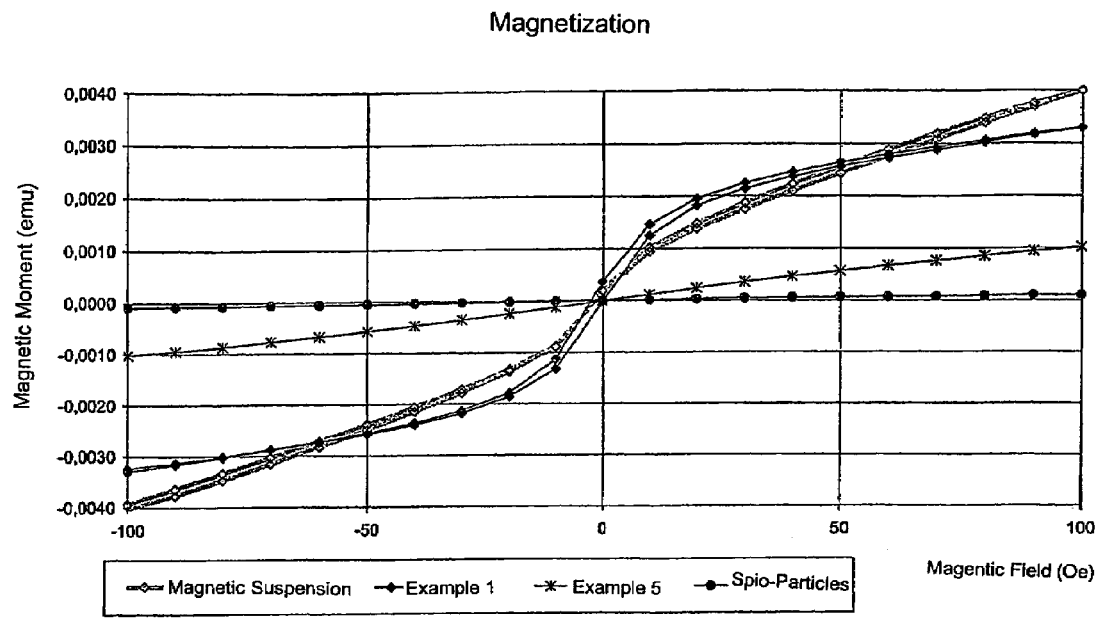
Figure 1. Measuring of magnetization of each 0,3mg particles in 60µl suspension
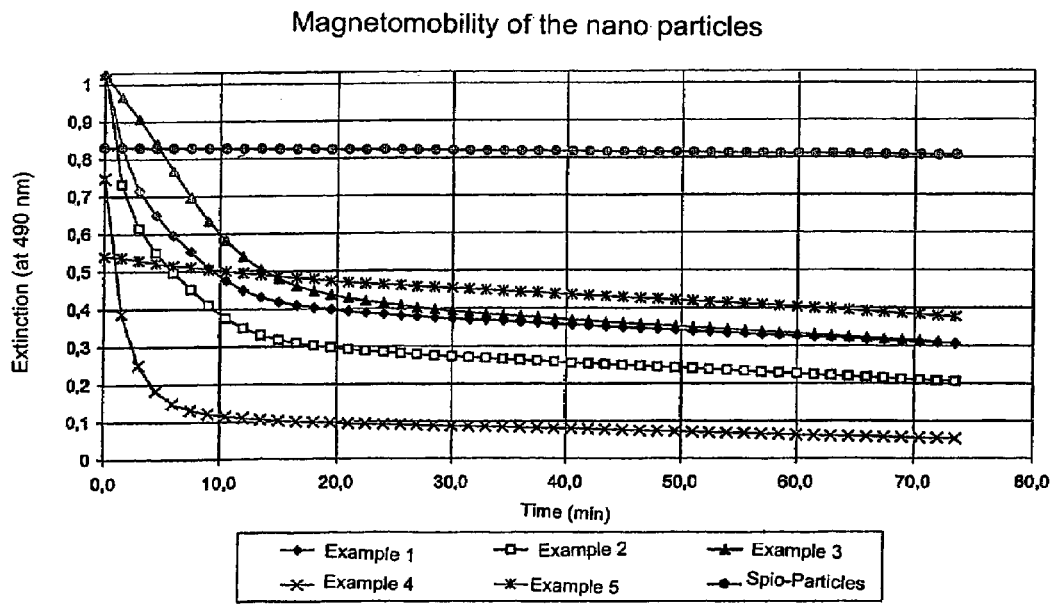
Figure 2. Measuring of the decrease of extinction of the nanoparticle suspensions (Examples 1-5) through separation of the particles on a permanent magnet in connection with time (wave length: 490 nm, iron concentration of particle suspensions: 60-70µg/mL).

MAGNETIC NANOPARTICLES HAVING IMPROVED MAGNETIC PROPERTIES

BACKGROUND OF THE INVENTION

The invention relates to a method for producing magnetic nanoparticles that comprise metal oxide polymer composites.

There are already a number of technically established applications for magnetic composite particles having diameters that can be measured in nanometers. For instance, such particles can be employed in molecular biological applications for isolating, fixing, and cleaning cells, cell constituents, nucleic acids, enzymes, antibodies, proteins, and peptides, in cellular biology for phagocytosis experiments, in clinical chemistry as a component of diagnostic assays or therapeutic pharmaceuticals, in clinical diagnostics as contrasting agents, radionuclide or drug carriers, in biochemistry and technical chemistry as solid phases for examining molecular recognition phenomena and heterogeneous catalytic processes.

A number of polymer-coated metal oxide particles for biological applications in magnetic fields have been described since the mid-1980s. In particular, magnetizable nanoparticles smaller than 200 nm unlock new possibilities for transporting and separating cells, cell constituents, bioactive molecules, and radionuclides (US2003/0099954 MILTENYI; WO01/17662 ZBOROWSKI; WO02/43708 ALEXIOU), for marking in contrasting magnetic imaging and diagnosis methods (US2003/0092029A1 JOSEPHSON; WO01/74245 JOHANSSON; U.S. Pat. No. 5,427,767 KRESSE), and the mechanical (DE10020376A1 KOCH) and thermal influencing of living cells (U.S. Pat. No. 6,541,039 LESNIAK) and have therefore been continuously improved in terms of their application-related properties. Common to all of the applications is the fact that magnetizable metal oxides having a biocompatible polymer coating to form composite particles having sizes from 5 nm to 500 nm are bound to a colloidally stable suspension with an aqueous base. The coating material should either prevent interaction with biological materials, facilitate good tolerance with living cells, and influence the paths for metabolization in living organisms, or should enable selective bonding to the surface using targeted functionalization with biochemically active substances, or should release enclosed substances in a controlled manner. An energetic interaction with external magnetic fields is used by means of the magnetizable portions of the composite particles. In magnetic fields, such particles, depending on the magnetic properties, experience an alignment and they move corresponding to physical magnetic field gradients and react to temporal changes in the external magnetic field. A great number of methods were described for producing iron oxide crystallites as metal oxide particles, for instance by sintering at high temperatures with subsequent mechanical comminution, cluster formation under vacuum conditions, or wet chemical synthesis from solutions. The precipitation of iron oxides can occur under non-aqueous conditions (U.S. Pat. No. 4,677,027 PORATH) and subsequently be converted to aqueous conditions (U.S. Pat. No. 5,160,725 PILGRIM) or can occur exclusively in aqueous solutions (U.S. Pat. No. 4,329,241 MASSART). An aqueous formulation is used for biological applications because of toxicological considerations (U.S. Pat. No. 4,101,435 HASEGAWA). Wet chemical synthesis of the iron oxide crystallites can precede coating with polymer components (core-shell method) or can occur in the presence of the polymer (one-pot method). The core-shell method requires that stabilizers be added to the iron oxides, since the latter tend to form aggregates in aqueous suspension. Stabilizers can be amphiphilic substances (WO01/56546 BABINCOVA) or additional nanoparticles with an electrically charged surface (U.S. Pat. No. 4,280,918 HOMOLA). Surface-active substances as stabilizers can severely limit the options for chemical functionalization of the surface, however. Today in general magnetizable nanocomposite particles containing iron that are produced primarily using the one-pot method are accepted for medical applications due to their physical and chemical properties and pharmaceutical/galenic stability. The one-pot method uses the coating polymer directly during the formation of the iron oxides for stabilization during nucleation and growth of the crystallites from the solution. One of the most frequently employed coating materials is dextrane in a number of modifications. However, other polysaccharides such as arabinogalactane, starch, glycosaminoglycanes, or proteins have also been used (U.S. Pat. No. 6,576,221 KRESSE). Precipitation of iron(II) and iron(III) salts in the presence of dextrane (U.S. Pat. No. 4,452,773 MOLDAY) is probably the simplest method. This method is modified by using ultrasound and subsequent thermal treatment in a flow-through method (U.S. Pat. No. 4,827,945 GROMAN). The quality of the product can be further improved using magnetic classification (WO9007380 MILTENYI). Further encapsulation/coating, generally while using amphiphilic substances as stabilizers, can substantially modify the behavior of biological systems with regard to the composite particles (U.S. Pat. No. 5,545,395 TOURNIER, EP0272091 ELEY).

For producing highly disperse aqueous systems as injectable liquid, special methods of homogenization are used in addition to various stabilizers. Such methods are for instance rotor/stator homogenization and high-pressure homogenization. Particularly high mechanical energy input is attained using liquid jet or a liquid slot-nozzle high-pressure homogenizers (micro fluidizer technology), which is used in particular for producing liposomes (U.S. Pat. No. 5,635,206 GANTER) but also in other cases facilitates the production of injectable active substance formulations (U.S. Pat. No. 5,595,687 RAYNOLDS). The use of a high-pressure homogenizers for producing oxidic nanocomposite particles by means of controlled coalescence with subsequent drying in emulsions whose non-aqueous components contain an oxide component as sol is described in conjunction with the industrial production of catalyst materials (U.S. Pat. No. 5,304,364 COSTA) and electrographic toner particles, ceramic powder, felt materials, spray coatings, active substance carriers, or ion exchange resins (U.S. Pat. No. 5,580,692 LOFFTUS).

None of the described magnetic particle types in the range of less than 200 nm can generally be concentrated or fixed without complex separating methods (e.g. high gradient magnet separation).

On the other hand, there are already numerous magnetic particle applications in the life sciences that could be performed with much greater efficiency using separating steps on permanent magnets or that require high magnetic mobility of the particles for other reasons.

SUMMARY OF THE INVENTION

Thus the object of the present invention was to provide magnetic nanoparticles that have sufficiently high magnetization at small field strengths.

This object is attained in that magnetic nanoparticles comprising a metal oxide or metal oxides and a polymer having a mass portion of metal that is greater than or equal to 50% and hydrodynamic diameters of less than 200 nm are produced from the components and a carrier medium by means of high pressure homogenization.

These magnetic nanoparticles are furthermore characterized in that they have a comparatively higher magnetic moment at small magnetic field strengths than the metal oxide used.

Such magnetic nanoparticles are not structured using amphiphilics, as is the case with magnetic liposomes, nor are they stabilized by tensides as is commonly done with ferrofluids. Rather, in water and aqueous solutions they form a colloid that is stable for a long period without the effect of an external magnetic field. The magnetic nanoparticles can be separated with permanent magnets from a medium where they are contained. For example, the magnetic nanoparticles can be separated from water or an aqueous solution where the magnetic nanoparticles have formed a colloid.

BRIEF DESCRIPTION OF THE SEVERAL VIEWS OF THE DRAWINGS

FIG. 1 shows the magnetization of particles.
FIG. 2 shows the magnetomobility of particles.

DETAILED DESCRIPTION OF THE INVENTION

The metal oxides primarily used are iron oxides such as magnetite ($Fe_3O_4$) or maghemite ($Fe_2O_3$) or mixed phases resulting therefrom. The iron oxides can certainly also contain portions of other bivalent or trivalent metal ions, such as for instance $Ca^{2+}$, $Ba^{2+}$, $Zn^{2+}$, $Co^{2+}$, $Co^{3+}$, $Cr^{3+}$, $Ti^{3+}$, $Mo^{2+}$, $Mn^{2+}$, and $Cu^{2+}$.

The polymer employed can come from the area of synthetic polymers. Principally polymers that have heteroatoms or functional groups and that can enter into binding interactions with metal ions are used for this, such as, among others, polyols, polyamines, polyethers, polyesters, polyamides, and derivatives, copolymers, and blends thereof.

On the other hand, the polymer can also be selected from the group of biopolymers and here in particular from the area of polysaccharides. Both natural and also derivatized polysaccharides can be used. Among the polysaccharides, a number of these have a pronounced affinity to heavy metal ions, in particular also iron ions.

Among these is also dextrane, which offers the additional advantage that it is less subject to fluctuations in quality than other natural polysaccharides (e.g. starch), which is very important in terms of the reproducibility of the particle charges. Likewise, dextrane can be derivatized in a number of ways. In accordance with one method that is known per se, functional groups (COOH, $NH_2$, . . . ) spacers with functional groups (polyethylene glycol-based COOH or $NH_2$ groups), or biochemically relevant substructures (oligonucleotides, nucleic acids, peptides, proteins, and antibodies and enzymes) can be inserted. However, derivatization of dextrane can also be used to bind metal-selective chelators, for instance for fixing radionuclides, or pharmaceutically active substances.

High pressure homogenization using the type M-110Y Microfluidizer™ has proved itself as a technology for producing the inventive magnetic nanoparticles. The metal oxide and polymer components are processed in a carrier medium—water is used in most cases—at pressures of 500 bar or more such as ranging from 500 bar to 1200 bar using high shear forces. The method can also be modified in that the metal oxides are not generated until during the ultrahomogenization from the corresponding metal salts or hydroxides in situ. In these cases an alkaline carrier medium is used, for instance an aqueous ammonia solution.

Surprisingly, it was possible to determine that the high-pressure homogenization of the metal oxide and polymer components in a carrier medium leads not only to a colloidally stable magnetic particle population in the mean range below 200 nm, but, moreover, that the magnetic particles produced at small magnetic field strengths below 50 Oe have greater magnetic moment than they would for the metal oxide used for the starting material (FIG 1).

The effect of the improved magnetic properties on magnetic mobility becomes clear when the values found for the inventively produced magnetic nanoparticles are compared to conventional super-paramagnetic iron oxide particles (SPIO) (FIG 2). The magnetic nanoparticles obtained in accordance with Examples 1 through 5 all have substantially higher magnetic mobilities than comparable SPIO particles (like U.S. Pat. No. 4,452,773, particle diameter: 100 nm).

The inventively produced magnetic nanoparticles can be used for a number of life sciences applications. For instance, they are particularly suitable for applications in the bioanalytic and diagnostic field, in bioseparation processes, and as carrier materials in high throughput screening. The small diameter in conjunction with pronounced colloidal stability furthermore allows their use for in vivo applications, for instance in the form of injectable contrasting agents, radionuclide carriers, or active substance depots. For such applications it is particularly advantageous that the inventive particles can be prepared using sterile filtration.

The invention shall be explained in greater detail using the following examples without being limited thereto.

EXAMPLE 1

36 g dextrane (MW=40,000 D, Fluka) were dissolved in 120 ml water. 18 ml of a 2.5% (w/w) aqueous magnetite suspension (micromod, 45-00-202, particle diameter: 200 nm) were heated to 40° C. and ultrahomogenized for 10 min at 500 bar in the M-110Y Microfluidizer. After increasing the pressure to 1000 bar, the dextrane solution that had been heated to 40° C. was added to the ultrahomogenized magnetite suspension. The dextrane/magnetite suspension was ultrahomogenized for 20 min at 1000 bar and 90° C. After cooling to room temperature, the magnetic nanoparticles obtained were separated on the permanent magnet for 15 min for separating the dextrane excess and re-suspended in 40 ml water. The hydrodynamic diameter of the resultant magnetic nanoparticles is 130-140 nm (photon correlation spectroscopy, Zetasizer 3000, Malvern Inst.). The iron portion in the particles is 58-62% (w/w).

EXAMPLE 2

Particle synthesis was performed as in Example 1, whereby the pressure during the entire ultrahomogenization was 500 bar. The hydrodynamic diameter of the resultant magnetic nanoparticles is 161-180 nm (photon correlation spectroscopy, Zetasizer 3000, Malvem Inst.). The iron portion in the particles is 58-62% (w/w).

EXAMPLE 3

Particle synthesis was performed as in Example 1, whereby the dextrane:magnetite mass ratio was raised from 8:1 (Example 1) to 12:1. For this, 54 g dextrane (MW=40,000 D, Fluka) were dissolved in 180 ml water. The hydrodynamic diameter of the resultant magnetic nanoparticles is 130-140 nm (photon correlation spectroscopy, Zetasizer 3000, Malvern Inst.). The iron portion in the particles is 52-56% (w/w).

EXAMPLE 4

12 g ethylene imine polymer solution (50% (v/v), MW=601-1,000 kD, Fluka) were mixed with 30 ml water. 60 ml of a 2.5% (w/w) aqueous magnetite suspension (micromod, 45-00-202, particle diameter: 200 nm) were heated to 40° C. and ultrahomogenized for 10 min at 500 bar in the M-110Y Microfluidizer. After increasing the pressure to 1000 bar, the ethylene imine polymer solution that had been heated to 40° C. was added to the ultrahomogenized magnetite suspension. The polyethylene imine/magnetite suspension was ultrahomogenized for 20 min at 1000 bar and 90° C. After cooling to room temperature, the magnetic nanoparticles obtained were separated on the permanent magnet for separating the polymer excess for 15 min and re-suspended in 25 ml water. The hydrodynamic diameter of the resultant magnetic nanoparticles is 80 nm (photon correlation spectroscopy, Zetasizer 3000, Malvern Inst.). The iron portion in the particles is 60-65% (w/w).

EXAMPLE 5

72 g dextrane (MW=40,000 D, Fluka) were dissolved in 180 ml water. 90 ml of a 1.5% (w/w) aqueous maghemite suspension (produced according to: M. Holmes, et. al., J. Magn. Magn. Mater. 122, 134 (1993), particle diameter: 20 nm, pH=1.6-2.0) were heated to 40° C. and ultrahomogenized for 5 min at 500 bar in the M-110Y Microfluidizer. After adding the dextrane solution that had been heated to 40° C. to the ultrahomogenized maghemite suspension, the suspension was neutralized by adding 120 ml 0.1 M sodium hydroxide. After cooling to room temperature, the magnetic nanoparticles obtained were washed with water by means of a high gradient magnetic field. The hydrodynamic diameter of the resultant magnetic nanoparticles is 60-70 nm (photon correlation spectroscopy, Zetasizer 3000, Malvern Inst.). The iron portion in the particles is 50-52% (w/w).

EXAMPLE 6

For functionalization with terminal carboxylic acid groups using an ethylene glycol spacer, 20 ml of a 5% (w/w) dextrane/magnetite nanoparticle suspension from Example 1 (particle diameter: 130-140 nm) were mixed with 5 ml 0.5 M 2-morpholinoethane sulfonic acid buffer (pH=6.3). 120 mg N-ethyl-N'-(3-dimethylaminopropyl)-carbodiimide hydrochloride and 120 mg 3,6-dioxaoctane diacid each were dissolved in 5 ml 0.1 M 2-morpholinoethane sulfonic acid buffer (pH=6.3) and combined. After incubating this solution for 10 minutes at 50° C., it was added to the nanoparticle suspension. The particle suspension was shaken for 2 hours at room temperature. After separation on the permanent magnet, the nanoparticles were resuspended in water. A value of 40-50 nmol/mg was found for the density of carboxylic acid groups on the particle surface by means of streaming potential measurement (polyelectrolyte titration against 0.001 N poly(diallyldimethyl ammonium chloride) solution, Mütek PCD 03 pH). The hydrodynamic diameter of the resultant magnetic nanoparticles is 120-130 nm (photon correlation spectroscopy, Zetasizer 3000, Malvern Instr.). The iron portion in the particles is 60-65% (w/w).

EXAMPLE 7

For covalent bonding of streptavidin to the particle surface, 10 ml of a 2% (w/w) dextrane/magnetite nanoparticle suspension from Example 6 having terminal carboxylic acid groups on the particle surface were mixed with 2.5 ml 0.5 M 2-morpholinoethane sulfonic acid buffer (pH=6.3). 20 mg N-ethyl-N'-(3-dimethylaminopropyl)-carbodiimide hydrochloride and 40 mg N-hydroxysuccinimide each were dissolved 0.1 M 2-morpholinoethane sulfonic acid buffer (pH=6.3) and added to the nanoparticle suspension. The particle suspension was shaken for 2 hours at room temperature. After separation on the permanent magnet, the nanoparticles were resuspended in 10 ml 0.1 M 2-morpholinoethane sulfonic acid buffer (pH=6.3). After adding 1 mg streptavidin (molecular probes), the particle suspension was shaken for 3 hours at room temperature. For saturating reactive places, after the addition of 2 ml 0.4 M glycin solution the particle suspension was shaken for another hour at room temperature. After separation on the permanent magnet, the nanoparticles were washed once with 10 ml PBS buffer (pH=7.4) and resuspended in 5 ml PBS buffer (pH=7.4). The concentration of covalently bound streptavidin on the dextrane/magnetite nanoparticles is 1.5-2 μg streptavidin per mg of particles. The hydrodynamic diameter of the resultant magnetic nanoparticles is 130-140 nm (photon correlation spectroscopy, Zetasizer 3000, Malvern (Instr.). The iron portion in the particles is 60-65% (w/w).

The invention claimed is:

1. Magnetic nanoparticles comprising iron oxide and a polymer and produced by subjecting the iron oxide and the polymer to high pressure homogenization in an aqueous medium, the nanoparticles comprising at least 50 mass percent iron, having hydrodynamic diameter of less than 200 nm and higher magnetization at low magnetic field strengths than the iron oxide from which the magnetic nanoparticles were produced.

2. Magnetic nanoparticles according to claim 1, wherein the nanoparticles have the properties of forming in water or an aqueous solution a colloid which is stable for a long period in the absence of an external magnetic field.

3. Magnetic nanoparticles according to claim 1, wherein the nanoparticles have the property of being separable by permanent magnets from a medium in which the nanoparticles are contained.

4. Magnetic nanoparticles according to claim 2 wherein the nanoparticles have the property of being separable from the water or the aqueous solution in which they have formed a colloid.

5. Magnetic nanoparticles according to claim 1, wherein the iron oxide comprises magnetite or maghemite or a mixture of magnetite and maghemite.

6. Magnetic nanoparticles according to claim 5, wherein the iron oxide or mixture of iron oxides contains at least one bivalent or trivalent metal ion other than iron ions.

7. Magnetic nanoparticles according to claim 1, wherein the polymer comprises synthetic polymer.

8. Magnetic nanoparticles according to claim 1, wherein the polymer comprises natural or derivatized polysaccharide.

9. Magnetic nanoparticles according to claim 8, wherein the polysaccharide comprises dextrane.

10. Magnetic nanoparticles according to claim 9, wherein the dextrane is derivatized with functional groups or substructures.

11. Magnetic nanoparticles comprising iron oxide and a polymer and produced by sequentially subjecting the iron oxide and a combination of iron oxide and polymer to high pressure homogenization in an aqueous medium, the nanoparticles comprising at least 50 mass percent iron, having hydrodynamic diameter of less than 200 nm and higher magnetization at low magnetic field strengths than the iron oxide from which the magnetic nanoparticles were produced, wherein the subjecting comprises the steps of:

providing an aqueous suspension of iron oxide in a high pressure homogenizer, homogenizing the suspension of iron oxide in the high pressure homogenizer at a pressure of 500 bar, combining an aqueous solution of a polymer with the homogenized suspension of iron oxide in the high pressure homogenizer, homogenizing the resulting combination in the high pressure homogenizer at a pressure of 500 to 1200 bar to form a suspension of the magnetic nanoparticles, and separating the magnetic nanoparticles from the suspension of magnetic nanoparticles under the action of a magnetic field.

12. The magnetic nanoparticles of claim 11 wherein the magnetic field in the separation step is provided by a permanent magnet.

13. Magnetic nanoparticles comprising iron oxide and a polymer and produced by subjecting the iron oxide to high pressure homogenization in an aqueous medium, the nanoparticles comprising at least 50 mass percent iron, having hydrodynamic diameter of less than 200 nm and higher magnetization at low magnetic field strengths than the iron oxide from which the magnetic nanoparticles were produced, wherein the subjecting comprises the steps of:

providing an aqueous suspension of iron oxide in a high pressure homogenizer, homogenizing the suspension of iron oxide in the high pressure homogenizer at a pressure of 500 bar, combining an aqueous solution of a polymer with the homogenized suspension of iron oxide in the high pressure homogenizer, adjusting the pH of the combined aqueous suspension of iron oxide and aqueous solution of polymer by adding an alkaline substance to obtain the magnetic nanoparticles, and washing the magnetic nanoparticles with water under the influence of a high gradient magnetic field.

14. The magnetic nanoparticles of claim 1 wherein the homogenization step is carried out at a pressure of 500 to 1200 bar.

15. The magnetic nanoparticles of claim 1 wherein the iron oxide is produced in situ in the aqueous medium, wherein the aqueous medium has a pH>7.

16. The magnetic nanoparticles of claim 15 wherein the aqueous medium comprises a solution of ammonia and water.

* * * * *